US012746411B2

(12) United States Patent
Belkin et al.

(10) Patent No.: US 12,746,411 B2
(45) Date of Patent: Sep. 29, 2026

(54) SELECTIVE LASER STIMULATION OF CORNEAL STEM CELLS

(71) Applicant: BELKIN VISION LTD., Yavne (IL)

(72) Inventors: Michael Belkin, Givat Shmu'el (IL); Zachary Sacks, Modiin (IL)

(73) Assignee: BELKIN VISION LTD., Yavne (IL)

( * ) Notice: Subject to any disclaimer, the term of this patent is extended or adjusted under 35 U.S.C. 154(b) by 1147 days.

(21) Appl. No.: 17/627,701

(22) PCT Filed: Sep. 7, 2020

(86) PCT No.: PCT/IB2020/058300
§ 371 (c)(1),
(2) Date: Jan. 17, 2022

(87) PCT Pub. No.: WO2021/048723
PCT Pub. Date: Mar. 18, 2021

(65) Prior Publication Data

US 2022/0249861 A1 Aug. 11, 2022

Related U.S. Application Data

(60) Provisional application No. 62/899,162, filed on Sep. 12, 2019.

(51) Int. Cl.
*A61F 9/008* (2006.01)
*A61B 3/117* (2006.01)
(Continued)

(52) U.S. Cl.
CPC .............. *A61N 5/067* (2021.08); *A61B 3/117* (2013.01); *A61F 9/008* (2013.01);
(Continued)

(58) Field of Classification Search
CPC ............ A61N 5/067; A61N 2005/0635; A61N 2005/0626; A61N 5/0622;
(Continued)

(56) References Cited

U.S. PATENT DOCUMENTS 2,635,502 A 4/1953 Richards
3,594,072 A 7/1971 Feather
(Continued)

FOREIGN PATENT DOCUMENTS

AU 2002951467 10/2002
AU 2015210430 A1 9/2015
(Continued)

OTHER PUBLICATIONS

Sridhar, MS. Anatomy of cornea and ocular surface. Indian J Ophthalmol. Feb. 2018; 66(2):190-194. doi: 10.4103/ijo.IJO_646_17. PMID: 29380756; PMCID: PMC5819093 (Year: 2018).*
(Continued)

*Primary Examiner* — Benjamin J Klein
*Assistant Examiner* — Alisha J Sircar
(74) *Attorney, Agent, or Firm* — Sanders IP Law

(57) ABSTRACT

Apparatus (20) for ophthalmic treatment includes an optical unit (30), which includes a camera (54), which is configured to capture an image of an eye (25) of a patient, a laser (48), which is configured to emit pulses of laser radiation, and beam conditioning and scanning optics (49, 50), which are configured to focus and direct the laser radiation to impinge on an anterior surface of the eye. A controller (44) is configured to analyze the image so as to identify a limbus of the eye, and to control the optical unit so that the laser radiation impinges on a set of one or more locations on the anterior surface of the eye that are in a vicinity of the limbus with a pulse duration and an energy selected so as to stem cells at the one or more locations.

8 Claims, 6 Drawing Sheets

(51) Int. Cl.
*A61N 5/067* (2006.01)
*A61N 5/06* (2006.01)

(52) U.S. Cl.
CPC ............... *A61F 2009/00861* (2013.01); *A61F 2009/00868* (2013.01); *A61F 2009/00897* (2013.01); *A61N 2005/0635* (2013.01)

(58) Field of Classification Search
CPC . A61N 2005/0648; A61B 3/117; A61F 9/008; A61F 2009/00861; A61F 2009/00868; A61F 2009/00897; A61F 9/009
See application file for complete search history.

(56) References Cited

U.S. PATENT DOCUMENTS 4,587,257 A 5/1986 DeSantis et al.
4,641,349 A 2/1987 Flom et al.
4,718,418 A 1/1988 L'Esperance
4,848,894 A 7/1989 Buser et al.
4,941,093 A 7/1990 Marshall et al.
4,966,452 A 10/1990 Shields et al.
5,049,147 A 9/1991 Danon
5,123,902 A 6/1992 Muller et al.
5,141,506 A 8/1992 York
5,151,909 A 9/1992 Davenport et al.
5,152,760 A 10/1992 Latina
5,370,641 A 12/1994 O'Donnell, Jr.
5,422,899 A 6/1995 Freiberg et al.
5,479,222 A 12/1995 Volk et al.
5,537,164 A * 7/1996 Smith .................... A61B 3/125 351/219
5,549,596 A 8/1996 Latina
5,598,007 A 1/1997 Bunce et al.
5,786,883 A 7/1998 Miller et al.
5,865,830 A 2/1999 Parel et al.
5,982,789 A 11/1999 Marshall et al.
6,027,216 A 2/2000 Guyton et al.
6,030,376 A 2/2000 Arashima et al.
6,033,396 A 3/2000 Huang et al.
6,059,772 A 5/2000 Hsia et al.
6,096,029 A 8/2000 O'Donnell, Jr.
6,099,521 A 8/2000 Shadduck
6,099,522 A 8/2000 Knopp et al.
6,146,375 A 11/2000 Juhasz et al.
6,159,202 A 12/2000 Sumiya et al.
6,210,399 B1 4/2001 Parel et al.
6,258,082 B1 7/2001 Lin
6,263,879 B1 7/2001 Lin
6,267,752 B1 7/2001 Svetliza
6,267,756 B1 7/2001 Feuerstein et al.
6,286,960 B1 9/2001 Tomita
6,319,274 B1 11/2001 Shadduck
6,325,792 B1 12/2001 Swinger et al.
6,414,980 B1 7/2002 Wang et al.
6,454,763 B1 9/2002 Motter et al.
6,514,241 B1 2/2003 Hsia et al.
6,530,916 B1 3/2003 Shimmick
6,569,104 B2 5/2003 Ono et al.
6,585,723 B1 7/2003 Sumiya
6,673,062 B2 1/2004 Yee et al.
6,676,655 B2 1/2004 McDaniel
6,685,317 B2 2/2004 Su et al.
6,698,886 B2 3/2004 Pollack et al.
6,736,806 B2 5/2004 Ruiz et al.
6,761,713 B2 7/2004 Teichmann
6,899,707 B2 5/2005 Scholler et al.
6,942,656 B2 9/2005 Pawlowski et al.
6,948,815 B2 9/2005 Neuberger
6,979,328 B2 12/2005 Baerveldt et al.
7,027,233 B2 4/2006 Goldstein et al.
7,252,661 B2 8/2007 Nguyen et al.
7,282,046 B2 10/2007 Simon
7,353,829 B1 4/2008 Wachter et al.
7,371,230 B2 5/2008 Webb et al.
7,693,259 B2 4/2010 Gertner
7,792,249 B2 9/2010 Gertner et al.
8,004,764 B2 8/2011 Artsyukhovich et al.
8,048,065 B2 11/2011 Grecu et al.
8,109,635 B2 2/2012 Allon et al.
8,160,113 B2 4/2012 Adams et al.
8,403,921 B2 3/2013 Palankar et al.
8,442,185 B2 5/2013 Gertner et al.
8,465,478 B2 6/2013 Frey et al.
8,475,433 B2 7/2013 Mrochen et al.
8,545,020 B2 10/2013 Liesfeld et al.
8,568,393 B2 10/2013 Palanker
8,630,388 B2 1/2014 Gertner et al.
8,679,100 B2 3/2014 Raksi et al.
8,708,491 B2 4/2014 Frey et al.
8,709,029 B2 4/2014 Griffis, III et al.
8,771,261 B2 7/2014 Andersen et al.
8,811,657 B2 8/2014 Teiwes et al.
8,845,625 B2 9/2014 Angeley et al.
8,903,468 B2 12/2014 Peyman
8,920,407 B2 12/2014 Raksi et al.
8,939,965 B2 1/2015 Liesfeld et al.
8,968,279 B2 3/2015 Arnoldussen
8,995,618 B2 3/2015 Gertner
9,055,896 B2 6/2015 Amthor et al.
9,192,780 B2 11/2015 McDaniel
9,220,407 B2 12/2015 Yam et al.
9,351,878 B2 5/2016 Muehlhoff et al.
9,480,599 B2 11/2016 Degani et al.
9,495,743 B2 11/2016 Angeley et al.
9,504,609 B2 11/2016 Kurtz
9,532,712 B2 1/2017 Liesfeld et al.
9,622,911 B2 4/2017 Rubinfeld et al.
9,782,232 B1 10/2017 Papac
9,849,032 B2 12/2017 Schuele et al.
9,849,034 B2 12/2017 Artsyukhovich et al.
9,877,633 B2 1/2018 Zhao et al.
9,889,043 B2 2/2018 Frey et al.
9,968,483 B2 5/2018 Takeda et al.
10,022,457 B2 7/2018 Peyman
10,064,757 B2 9/2018 Berlin
10,143,590 B2 12/2018 Dick et al.
10,244,991 B2 4/2019 Shademan et al.
10,258,507 B2 4/2019 Gonzalez et al.
10,278,865 B2 5/2019 Luttrull et al.
10,299,961 B2 5/2019 Luttrull et al.
10,363,169 B2 7/2019 Belkin et al.
10,441,465 B2 10/2019 Hart et al.
10,449,091 B2 10/2019 Angeley et al.
10,456,209 B2 10/2019 Peyman
10,478,342 B2 11/2019 Dick et al.
10,524,656 B2 1/2020 Wiltberger et al.
10,617,564 B1 4/2020 Andersen et al.
10,684,449 B2 6/2020 Curatu et al.
10,702,416 B2 7/2020 Belkin et al.
10,849,789 B2 12/2020 Dewey et al.
10,925,768 B2 2/2021 Charles
11,564,836 B2 1/2023 Belkin et al.
11,890,051 B2 2/2024 Heacock
12,109,149 B2 10/2024 Sacks et al.
2001/0027314 A1 10/2001 Peyman
2002/0013572 A1 1/2002 Berlin
2002/0013573 A1 1/2002 Telfair et al.
2002/0026179 A1 2/2002 Toh
2003/0179344 A1 9/2003 Van de Velde
2003/0225398 A1 12/2003 Zepkin et al.
2004/0039378 A1 2/2004 Lin
2004/0059321 A1 3/2004 Knopp et al.
2004/0196431 A1* 10/2004 Farberov ................ A61B 3/117 351/205
2005/0096639 A1 5/2005 Slatkine et al.
2005/0107774 A1 5/2005 Lin
2005/0185138 A1 8/2005 Wong et al.
2005/0197655 A1 9/2005 Telfair et al.
2005/0254009 A1 11/2005 Baker et al.
2005/0286019 A1 12/2005 Wiltberger et al.
2005/0288745 A1* 12/2005 Andersen ............ A61F 9/00781 607/86
2006/0100677 A1 5/2006 Blumenkranz et al.

(56) References Cited

U.S. PATENT DOCUMENTS

2006/0176913 A1 8/2006 Souhaite et al.
2006/0195076 A1 8/2006 Blumenkranz et al.
2006/0224147 A1 10/2006 Abe et al.
2006/0265030 A1 11/2006 McDaniel
2007/0081166 A1 4/2007 Brown et al.
2007/0129709 A1 6/2007 Andersen et al.
2007/0159600 A1 7/2007 Gil et al.
2007/0213693 A1 9/2007 Plunkett
2008/0027418 A1 1/2008 Berry
2008/0089481 A1 4/2008 Gertner
2008/0108934 A1 5/2008 Berlin et al.
2008/0161781 A1 7/2008 McArdle et al.
2008/0167642 A1 7/2008 Palanker et al.
2008/0204658 A1 8/2008 Van Saarloos
2008/0234667 A1 9/2008 Lang et al.
2008/0255546 A1 10/2008 Orbachevski
2008/0319427 A1 12/2008 Palanker
2009/0137993 A1 5/2009 Kurtz
2009/0157062 A1 6/2009 Hauger et al.
2009/0161827 A1 6/2009 Gertner et al.
2009/0247997 A1 10/2009 Watanabe et al.
2010/0002837 A1 1/2010 Gertner et al.
2010/0057059 A1 3/2010 Makino
2010/0076419 A1 3/2010 Chew et al.
2010/0142767 A1 6/2010 Fleming
2010/0324543 A1 12/2010 Kurtz et al.
2011/0144627 A1 6/2011 Smith et al.
2011/0172649 A1 7/2011 Schuele et al.
2011/0190741 A1 8/2011 Deisinger et al.
2011/0202046 A1* 8/2011 Angeley ................. A61F 9/009 606/6
2012/0016349 A1 1/2012 Brownell
2012/0050308 A1 3/2012 Nakano et al.
2012/0083772 A1 4/2012 Rubinfeld et al.
2012/0089134 A1 4/2012 Horvath et al.
2012/0259321 A1 10/2012 Vera et al.
2012/0283557 A1 11/2012 Berlin
2013/0103011 A1 4/2013 Grant et al.
2013/0123761 A1* 5/2013 Belkin ................ A61F 9/00817 606/6
2013/0204236 A1 8/2013 Awdeh
2013/0218145 A1 8/2013 Belkin et al.
2013/0289450 A1 10/2013 Homer
2013/0317570 A1 11/2013 Luttrull et al.
2014/0094785 A1 4/2014 Charles
2014/0114297 A1 4/2014 Woodley et al.
2014/0128731 A1 5/2014 Gonzalez et al.
2014/0128851 A1 5/2014 Wysopal
2014/0128852 A1 5/2014 Gooding et al.
2014/0135747 A1 5/2014 Donitzky et al.
2014/0135753 A1 5/2014 Feklistov et al.
2014/0228824 A1 8/2014 Yee et al.
2014/0276681 A1 9/2014 Schuele et al.
2014/0307077 A1 10/2014 Prabhakar
2015/0157498 A1* 6/2015 Luttrull ............... A61F 9/00821 606/4
2015/0164635 A1 6/2015 Renke
2015/0223683 A1 8/2015 Davidovics et al.
2015/0266706 A1 9/2015 Hashimoto
2015/0272782 A1 10/2015 Schuele et al.
2015/0313759 A1 11/2015 Vera et al.
2015/0366706 A1 12/2015 Belkin et al.
2016/0008169 A1 1/2016 Yu
2016/0008172 A1 1/2016 Kahook
2016/0067035 A1 3/2016 Gontijo et al.
2016/0067087 A1 3/2016 Tedford et al.
2016/0089269 A1 3/2016 Horvath et al.
2016/0095752 A1 4/2016 Srinivasan et al.
2016/0113816 A1 4/2016 Herekar et al.
2016/0346126 A1 12/2016 Luttrull et al.
2016/0354241 A1 12/2016 Mordaunt et al.
2016/0367399 A1 12/2016 Goldshleger et al.
2017/0000647 A1* 1/2017 Schuele .............. A61F 9/00825
2017/0038284 A1 2/2017 Nemati
2017/0087014 A1 3/2017 Potter, Jr. et al.
2017/0112663 A1* 4/2017 Bareket ................... A61F 9/008
2017/0127938 A1 5/2017 Izatt et al.
2017/0184875 A1 6/2017 Newman
2017/0246033 A1 8/2017 Bor et al.
2017/0281405 A1 10/2017 Ha
2017/0340483 A1 11/2017 Rill et al.
2017/0360604 A1 12/2017 Bach et al.
2018/0085257 A1 3/2018 Horvath et al.
2018/0104477 A1 4/2018 Kurtz et al.
2018/0125708 A1 5/2018 Bohme et al.
2018/0168737 A1 6/2018 Ren et al.
2018/0207029 A1 7/2018 Herekar et al.
2018/0214305 A1 8/2018 Schuele et al.
2018/0221199 A1 8/2018 Heacock
2018/0229051 A1 8/2018 Chen
2018/0235462 A1 8/2018 Gooi et al.
2018/0344527 A1 12/2018 Palanker et al.
2019/0078073 A1 3/2019 Streeter et al.
2019/0099291 A1 4/2019 Herekar et al.
2019/0105200 A1 4/2019 Hipsley
2019/0105519 A1 4/2019 Herekar et al.
2019/0117459 A1 4/2019 Berlin
2019/0142636 A1* 5/2019 Tedford ................ A61F 9/0079 606/4
2019/0151146 A1 5/2019 Kim
2019/0247225 A1 8/2019 Stobrawa et al.
2019/0269554 A1 9/2019 Goldshleger et al.
2019/0343680 A1 11/2019 Belkin et al.
2019/0344076 A1 11/2019 Yazoqui et al.
2019/0358085 A1 11/2019 Fu et al.
2020/0000638 A1 1/2020 Herekar et al.
2020/0038241 A1* 2/2020 Wang .................. A61F 9/00814
2020/0038245 A1 2/2020 Hart et al.
2020/0078216 A1 3/2020 Raksi
2020/0093639 A1 3/2020 McCall, Jr.
2020/0107724 A1 4/2020 Wiltberger et al.
2020/0146887 A1 5/2020 Horvath et al.
2020/0306080 A1 10/2020 Herekar et al.
2020/0345546 A1 11/2020 Belkin et al.
2020/0352785 A1 11/2020 Holland et al.
2020/0360187 A1 11/2020 Schuele et al.
2020/0379216 A1 12/2020 Curatu et al.
2021/0113373 A1 4/2021 Sacks et al.
2021/0267800 A1 9/2021 Sacks et al.
2021/0338484 A1 11/2021 Hipsley
2022/0031503 A1 2/2022 Dorin et al.
2023/0201037 A1 6/2023 Barrett et al.
2023/0226372 A1 7/2023 Herekar et al.

FOREIGN PATENT DOCUMENTS

AU 2015315113 B2 3/2016
CA 2640203 A1 8/2007
CN 1579351 A 2/2005
CN 1650148 A 8/2005
CN 101411607 A 4/2009
CN 101657165 A 2/2010
CN 201537172 U 8/2010
CN 102193182 A 9/2011
CN 102497833 A 6/2012
CN 102811684 A 12/2012
CN 103917150 A 7/2014
CN 103997948 A 8/2014
CN 105050556 A 11/2015
CN 105138996 A 12/2015
CN 106102629 A 11/2016
CN 106163467 A 11/2016
CN 205698218 U 11/2016
DE 202016006265 U1 3/2017
EP 0224322 A1 6/1987
EP 0651982 A1 5/1995
EP 0689811 A1 1/1996
EP 1602321 A1 12/2005
EP 2301421 A1 3/2011
EP 2301424 B1 3/2011
EP 2301425 B1 3/2011
EP 2602005 A1 6/2013
EP 1856774 B1 6/2016
EP 2695016 B1 3/2017

(56) References Cited

FOREIGN PATENT DOCUMENTS

| | | | |
|---|---|---|---|
| EP | 2992931 | B1 | 8/2017 |
| EP | 2391318 | B1 | 12/2017 |
| EP | 3329839 | A1 | 6/2018 |
| EP | 2729099 | B1 | 11/2019 |
| EP | 3191040 | B1 | 7/2020 |
| EP | 3517081 | B1 | 11/2020 |
| EP | 2854729 | B1 | 3/2021 |
| FR | 2655837 | A1 | 6/1991 |
| JP | H09506521 | A | 6/1997 |
| JP | 2007151739 | A | 6/2007 |
| JP | 2008539824 | A | 11/2008 |
| JP | 2010148635 | A | 7/2010 |
| JP | 2015530898 | A | 10/2015 |
| JP | 2016013255 | A | 1/2016 |
| JP | 2016508799 | A | 3/2016 |
| JP | 2017530774 | A | 10/2017 |
| JP | 2018051210 | A | 4/2018 |
| KR | 20180106113 | A | 10/2018 |
| KR | 20190022216 | A | 3/2019 |
| RU | 2499582 | C1 | 11/2013 |
| RU | 2553507 | C1 | 6/2015 |
| WO | 9216259 | A1 | 10/1992 |
| WO | 1993012727 | A1 | 7/1993 |
| WO | 9316631 | A1 | 9/1993 |
| WO | 9412092 | A1 | 6/1994 |
| WO | 9416425 | A1 | 7/1994 |
| WO | 9515134 | A1 | 6/1995 |
| WO | 1998022016 | A2 | 5/1998 |
| WO | 9918868 | A1 | 4/1999 |
| WO | 0195842 | A1 | 12/2001 |
| WO | 02064031 | A2 | 8/2002 |
| WO | 02087442 | A1 | 11/2002 |
| WO | 2014018104 | A1 | 1/2004 |
| WO | 2004027487 | A1 | 4/2004 |
| WO | 2006119349 | A2 | 11/2006 |
| WO | 2006119584 | A1 | 11/2006 |
| WO | 2006128038 | A2 | 11/2006 |
| WO | 2007103349 | A2 | 9/2007 |
| WO | 2008112236 | A1 | 9/2008 |
| WO | 2008118198 | A2 | 10/2008 |
| WO | 2009039315 | A2 | 3/2009 |
| WO | 2010094353 | A1 | 8/2010 |
| WO | 2010113193 | A1 | 10/2010 |
| WO | 2011017002 | A2 | 2/2011 |
| WO | 2011163508 | A2 | 6/2011 |
| WO | 2011085274 | A1 | 7/2011 |
| WO | 2011151812 | A1 | 12/2011 |
| WO | 2013004255 | A1 | 1/2013 |
| WO | 2013035091 | A1 | 3/2013 |
| WO | 2013059481 | A1 | 4/2013 |
| WO | 2013059564 | A1 | 4/2013 |
| WO | 2013122711 | A1 | 8/2013 |
| WO | 2013165689 | A1 | 11/2013 |
| WO | 2014025862 | A1 | 2/2014 |
| WO | 2014132162 | A1 | 9/2014 |
| WO | 2014191031 | A1 | 12/2014 |
| WO | 2015069197 | A1 | 5/2015 |
| WO | 2015130821 | A2 | 9/2015 |
| WO | 2016018864 | A1 | 2/2016 |
| WO | 2016058931 | A2 | 4/2016 |
| WO | 2016156760 | A1 | 10/2016 |
| WO | 2016187436 | A1 | 11/2016 |
| WO | 2016207739 | A1 | 12/2016 |
| WO | 2017023296 | A1 | 2/2017 |
| WO | 2017031570 | A1 | 3/2017 |
| WO | 2017069819 | A1 | 4/2017 |
| WO | 2018005796 | A1 | 1/2018 |
| WO | 2018021780 | A1 | 2/2018 |
| WO | 2018049246 | A1 | 3/2018 |
| WO | 2018152020 | A1 | 8/2018 |
| WO | 2018232397 | A1 | 12/2018 |
| WO | 2019109125 | A1 | 6/2019 |
| WO | 2019173759 | A1 | 9/2019 |
| WO | 2020008323 | A1 | 1/2020 |
| WO | 2020012841 | A1 | 1/2020 |
| WO | 2020018242 | A1 | 1/2020 |
| WO | 2020018436 | A1 | 1/2020 |
| WO | 2020050308 | A1 | 3/2020 |
| WO | 202093060 | A2 | 5/2020 |
| WO | 2020089737 | A1 | 5/2020 |
| WO | 2020183342 | A1 | 9/2020 |
| WO | 2021026538 | A1 | 2/2021 |
| WO | 2021048723 | A1 | 3/2021 |
| WO | 2021155445 | A1 | 8/2021 |
| WO | 2021170664 | A1 | 9/2021 |
| WO | 2022223690 | A1 | 10/2022 |

OTHER PUBLICATIONS

International Application # PCT/IB2023/061472 Search Report dated Feb. 29, 2024.

Nagar et al., "A randomised, prospective study comparing selective laser trabeculoplasty with latanoprost for the control of intraocular pressure in ocular hypertension and open angle glaucoma," British Journal of Ophthalmology, vol. 89, pp. 1413-1417, year 2005.

Hong et al., "Repeat Selective Laser Trabeculoplasty," Journal of Glaucoma, vol. 18, issue 3, pp. 180-183, Mar. 2009.

Goyal et al., "Effect of primary selective laser trabeculoplasty on tonographic outflow facility—a randomised clinical trial," British Journal of Ophthalmology, BMJ Publishing Group, vol. 94, issue 11, pp. 1-22, year 2010.

Franco et al., "Effect of Second SLT on IOP," Investigative Ophthalmology & Visual Science, vol. 48, pp. 1-2, May 2007.

Chen et al., "A Comparison between 90 degrees and 180 degrees Selective Laser Trabeculoplasty," Journal of Glaucoma, vol. 13, issue 1, p. 1, Feb. 2004.

Mequio et al., "Efficacy of Repeat Selective Laser Trabeculoplasty," Investigative Ophthalmology & Visual Science, vol. 48, p. 1, year 2007.

Grulkowski et al., "Anterior segment imaging with Spectral OCT system using a high-speed CMOS camera," Optics Express, vol. 17, No. 6, p. 4842-4858, year 2009.

Shields et al., "Noncontact Transscleral ND:YAG Cyclophotocoagulation: A Long-Term Follow-Up of 500 Patients," Transactions of the American Ophthalmological Society, vol. XCII, pp. 271-287, year 1994.

Liu et al., "Real-time visual analysis of microvascular blood flow for critical care," CVPR2015 paper as Open Access Version, provided by the Computer Vision Foundation, pp. 2217-2225, year 2015.

Desco et al., "Effect of prophylactic brimonidine on bleeding complications after cataract surgery," European Journal of Ophthalmology, vol. 15, pp. 228-232, year 2005.

Pasquali et al., "Dilute brimonidine to improve patient comfort and subconjunctival hemorrhage after LASIK," Journal of Refractive Surgery, vol. 29, pp. 469-475, year 2013.

Sacks et al., "Non-contact direct selective laser trabeculoplasty: light propagation analysis," Biomedical Optics Express, vol. 11, pp. 2889-2904, year 2020.

Kasuga et al., "Trabecular Meshwork Length in Men and Women by Histological Assessment," Current Eye Research, Early Online, pp. 1-5, Jun. 2012.

International Application # PCT/IB2020/058300 Search Report dated Dec. 27, 2020.

SensoMotoric Instruments GmbH (SMI), "SG 3000", Product Flyer, pp. 1-2, year 2010.

Ashik et al., "The precision of ophthalmic biometry using calipers," Canadian Journal of Ophthalmology, vol. 48, Issue 6, pp. 1-13, Dec. 2013.

Balalzsi, "Noncontact Thermal Mode Nd:YAG Laser Transscleral Cyclocoagulation in the Treatment of Glaucoma," Ophthalmology, vol. 98, pp. 1858-1863, year 1991.

Leung et al., "Anterior chamber angle imaging with optical coherence tomography," Eye, vol. 25, pp. 261-267, year 2011.

Tasman et al., "The Wills Eye Hospital Atlas of Clinical Ophthalmology," Lippincott Williams & Wilkins, p. 158, year 2001.

(56) References Cited

OTHER PUBLICATIONS

Gaasterland, "Laser Therapies: Iridotomy, Iridoplasty, and Trabeculoplasty," as appears in "The Glaucoma Book: A Practical Evidence-Based Approach to Patient Care," Springer, p. 722, year 2010.
Kara, "Bleeding in Retinal Images Using Image Processing", A Thesis submitted to the graduate school of applied sciences of Near East University, Nicosia, Larnaca, pp. 1-79, year 2019.
Navilas Operator Manual, Document Version 2.10, 2012 OD-OS GmbH, pp. 1-94, Sep. 2012.
Danielson et al., Fixed High-Energy versus Standard Titrated Energy Settings for Selective Laser Trabeculoplasty, Journal of Glaucoma Publish Ahead of Print, Wolters Kluwer Health, Inc., pp. 1-16, year 2023.
Radcliffe et al., "Energy Dose-Response in Selective Laser Trabeculoplasty: A Review," Journal of Glaucoma, vol. 31, pp. e49-e68, year 2022.
Gazzard, "A Brief Guide to Gonioscopy," Video Clip, Optometry today, pp. 1-2, May 21, 2015, as downloaded from https://www.youtube.com/watch?v=8yTTbHWxUik.
Alward et al., "Principles of Gonioscopy," Color Atlas of Gonioscopy, American Academy of Opthalmology, pp. 1-10, Nov. 8, 2017, as downloaded from https://www.aao.org/education/disease-review/principles-of-gonioscopy.
Nolan et al., "Gonioscopy skills and techniques," Community Eye Health Journal, vol. 34, No. 112, pp. 40-42, year 2021.
Breazzano et al., "Analysis of Schwalbe's Line (Limbal Smooth Zone) by Scanning Electron Microscopy and Optical Coherence Tomography in Human Eye Bank Eyes," Journal of Ophthalmic and Vision Research, vol. 8, issue 1, pp. 9-16, Jan. 2013.
Thorlabs, Inc., "CPS520—Collimated Laser Diode Module, 520 nm, 4.5 mW, Elliptical Beam, Ø11 mm," Product Details, pp. 1-1, years 1999-2023, as downloaded from https://www.thorlabs.com/thorproduct.cfm?partnumber=CPS520.
Prophotonix, "Green Laser Modules," Product Information, pp. 1-8, year 2024, as downloaded from https://www.prophotonix.com/led-and-laser-products/laser-modules/laser-modules-color/green-laser-modules/.
Idex Helath & Science LLC, "532 nm StopLine® single-notch filter," Product Details, pp. 1-2, year 2023 as downloaded from https://www.idex-hs.com/store/product-detail/nf03_532e_25/fl-009362?cat_id=products&node=individual_optical_filters.
Brackley et al., "Lecture: Using the Slit Lamp Microscope to Visualize the Ocular Structures," Video Clip, pp. 1-2, Sep. 17, 2022, as downloaded from https://www.youtube.com/watch?v=1E-sEhy9tBo.
Bruce et al., "Zoom in on Gonioscopy," Review of Optometry, pp. 1-8, Sep. 1, 2016, as downloaded from https://www.reviewofoptometry.com/article/zoom-in-on-gonioscopy.
AU Application # 2022211843 Office Action dated Jan. 8, 2024.
JP Application # 2022508451 Office Action dated Mar. 5, 2024.
AU Application # 2021369792 Office Action dated Mar. 21, 2024.
Kohnen et al., "Internal Anterior Chamber Diameter using Optical Coherence Tomography Compared with White-To- White Distances using Automated Measurements," Journal of Cataract & Refractive Surgery, vol. 32, pp. 1809-1813, Nov. 2006.
Zhang et al., "Perioperative Medications for Preventing Temporarily Increased Intraocular Pressure after Laser Trabeculoplasty (Review)," Cochrane Database of Systematic Reviews 2017, issue 2, pp. 1-117, year 2017.
Katta et al., "Optical Coherence Tomography Image-Guided Smart Laser Knife for Surgery," Lasers in Surgery and Medicine, Wiley Online Library, pp. 1-11, Jul. 2017.
Barnes et al., "Control of Intraocular Pressure Elevations after Argon Laser Trabeculoplasty: Comparison of Brimonidine 0.2% to Apraclonidine 1.0%," Opthalmology, vol. 106, No. 10, pp. 2033-2037, year 1999.
Yakopson et al., "Brimonidine 0.1% vs. Apraclonidine 0.5% for Prevention of Intraocular Pressure Elevation after Selective Laser Trabeculoplasty," Investigative Ophthalmology & Visual Science, vol. 49, p. 1234, May 2008.
Kim et at., "Effect of Prophylactic Topical Brimonidine (0.15%) Administration on the Development of Subconjunctival Hemorrhage after Intravitreal Injection," Retina, The Journal for Retinal and Vitreous Diseases, vol. 31, No. 2, pp. 389-392, year 2011.
Hong et al., "Effect of Prophylactic Brimonidine Instillation on Bleeding during Strabismus Surgery in Adults," American Journal of Ophthalmology, vol. 144, No. 3, pp. 469-470, Sep. 2007.
Goldsmith et al., "Anterior Chamber Width Measurement by High-Speed Optical Coherence Tomography," Ophthalmology, vol. 112, No. 2, pp. 238-244, year 2005.
Norden, "Effect of Prophilactic Brimonidine on Bleeding Complications and Flap Adherence After Laser in situ Keratomileusis," Journal of Refractive Surgery, vol. 18, No. 4, pp. 468-471, Jul./Aug. 2002.
SG Application # 11202010437T Office Action dated May 13, 2022.
U.S. Appl. No. 16/935,236 Office Action dated Jun. 16, 2022.
EP Application # 19877990.2 Search Report dated Jul. 5, 2022.
U.S. Appl. No. 17/427,926 Office Action dated May 9, 2024.
EP Application # 19877990.2 Office Oction dated May 13, 2024.
EP Application # 24158977.9 Search Report dated May 15, 2024.
EP Applicatian # 21845437.9 Search Report dated Jun. 19, 2024.
JP Application # 2023217477 Office Action dated Jul. 9, 2024.
U.S. Appl. No. 17/273,323 Office Action dated Jun. 18, 2024.
International Application # PCT/IB2021/059821 Search Report dated Apr. 7, 2022.
IN Application # 202117029897 Office Action dated Mar. 10, 2022.
EP Application # 19830473.5 Search Report dated Feb. 28, 2022.
Vogel et al., "Optical properties of human sclera, and their consequences for transscleral laser applications.", Lasers In Surgery and Medicine , vol. 11, pp. 331-340,year 1991.
Geffen et al., "Transscleral Selective Laser Trabeculoplasty Without a Gonioscopy Lens", Journal of Glaucoma, Inc, vol. 26, No. 3, pp. 201-207, Mar. 2017.
Das et al., "Sclera Recognition—A Survey", 2nd IAPR Asian Conference on Pattern Recognition, pp. 1-5, year 2013.
Kaya et al., "Designing A Pattern Stabilization Method Using Scleral Blood Vessels For Laser Eye Surgery", International Conference on Pattern Recognition, pp. 698-701, Istanbul, Turkey, Aug. 23-26, 2010.
Barkana et al., "Selective Laser Trabeculoplasty", Survey of Ophthalmology, vol. 52, No. 6, pp. 634-653, year 2007.
Arany, "Photobiomodulation therapy: Easy to do, but difficult to get right", LaserFocusWorld, pp. 1-6, Jul. 31, 2019 downloaded from www.laserfocusworld.com/lasers-sources/article/14037967/photobiomodulation-therapyeasy-to-do-put-difficult-to-get-right, pp. 22-24, year 2019.
Borzabadi-Farahani, "Effect of low-level laser irradiation on proliferation of human dental mesenchymal stem cells; a systemic review", Journal of Photochemistry and Photobiology B: Biology, vol. 162, pp. 577-582, Sep. 2016.
Acott et al., "Trabecular Repopulation by Anterior Trabecular Meshwork Cells After Laser Trabeculoplasty", American Journal of Ophthalmology, vol. 107, issue 1, pp. 1-6, Jan. 1989.
Cao et al., "Peripheral Iridotomy," Medscape 25, pp. 1-12, Jun. 15, 2020.
Husain, "Laser Peripheral Iridotomy—Practical Points", YouTube presentation, p. 1, Sep. 28, 2016, downloaded from https://www.youtube.com/watch ?=Azxzsv31yls.
Vandic et al., "Early Diagnosis of Ocular Hypertension Using a Low-Intensity Laser Irradiation Test", Photomedicine and Laser Surgey, vol. 00, No. 00, pp. 1-5, year 2009.
Smith et al., "Light scatter from the central human cornea", Journal "Eye", issue 4, pp. 584-588, year 1990.
Turati et al., "Patterned Laser Trabeculoplasty", Ophthalmic Surgery, Lasers and Imaging , vol. 41, No. 5, pp. 538-545, 2010.
Nozaki et al., "Patterned Laser Trabeculoplasty with PASCAL streamline 577", Investigative Ophthalmology & Visual Science, vol. 54, p. 1867, Jun. 2013.

(56) References Cited

OTHER PUBLICATIONS

Acktar, "Magic Black Coatings", Product Information, pp. 1-6, year 2017.
Acktar, "Fractal Black Coating", Product Information, pp. 1-5, year 2017.
Cloudy Nights LLC, "Cloudy Nights—Equipment Discussions—ATM", Optics and DIY Forum, pp. 1-5, Feb. 15, 2015.
Defense Tech, "Anti-Laser Contact Lenses", Product Information, p. 1-1, Nov. 29, 2004.
EC standard 60825-1, "Safety of Laser Products", Edition 1.2, pp. 1-122, years 2001-2008.
Laser Safety Industries, "Filter Specifications", pp. 1-5, year 2008.
Thorlabs, "Laser Safety Glasses", Product Information, p. 1, Nov. 3, 2014.
Surrey Nanosystems Ltd, "Vantablack", Data Sheet, pp. 1-4, Mar. 1, 2016.
CN Application # 2020800163407 Office Action dated Feb. 4, 2023.
JP Application # 2020561860 Office Action dated Feb. 7, 2023.
Gophotonics, "NL200 series," Data Sheet, pp. 1-3, Jun. 29, 2017.
EP Application # 20201567.3 Office Action dated Jun. 6, 2023.
JP Application # 2020561860 Office Action dated Jun. 13, 2023.
JP Application # 2021516473 Office Action dated Jun. 20, 2023.
CN Application # 2020800563096 Office Action dated Jul. 1, 2023.
EP Application # 20864109.2 Search Report dated Aug. 10, 2023.
Gazzard et al., "Selective Laser Trabeculoplasty versus Drops for Newly Diagnosed Ocular Hypertension and Glaucoma: The LiGHT RCT," Health Technology Assessment, NHS, vol. 23, issue 31, pp. 1-132, Jun. 2019.
Kelley et al., "Stem Cells in the Trabecular Meshwork: Present and Future Promises," Experimental Eye Research, vol. 88, issue 4, pp. 747-751, Apr. 2009.
Dueker et al., "Stimulation of Cell Division by Argon and Nd:YAG Laser Trabeculoplasty in Cynomolgus Monkeys," Investigative Ophthalmology & Visual Science, vol. 31, No. 1, pp. 115-124, year 1990.
Nowell et al., "Corneal Epithelial Stem Cells and their Niche at a Glance," Cell Science at a Glance, vol. 130, Issue 6, pp. 1021-1025, year 2017.
Kim et al., "Diagnosis of Corneal Limbal Stem Cell Deficiency," Current Opinion in Ophthalmology, Wolters Kluwer Health, Inc., vol. 28, No. 4, pp. 355-362, Jul. 2017.
Gonzalez et al., "Limbal Stem Cells: Identity, Developmental Origin, and Therapeutic Potential," WIREs Developmental Biology, Wiley, vol. 7, issue 2, pp. 1-23, Mar. 2018.
Sepehr, "Corneal Endothelial Cell Dysfunction: Etiologies and Management," Therapeutic Advances in Opthalmology, pp. 1-19, year 2018.
Espana et al., "Existence of Corneal Endothelial Slow-Cycling Cells," Investigative Ophthalmology & Visual Science, vol. 56, No. 6, pp. 3827-3837, Jun. 2015.
Walshe et al., "Serial Explant Culture Provides Novel Insights into the Potential Location and Phenotype of Corneal Endothelial Progenitor Cells," Experimental Eye Research, vol. 127, pp. 9-13, year 2014.
Pinnamaneni et al., "Concise Review: Stem Cells in the Corneal Stroma," Stem Cells, vol. 30, issue 6, pp. 1059-1063, year 2012.
U.S. Appl. No. 16/935,236 Office Action dated Nov. 7, 2022.
EP Application # 20769533.9 Search Report dated Nov. 8, 2022.
AU Application # 2020345067 Office Action dated Nov. 30, 2022.
CN Application # 201980070459X Office Action dated Dec. 23, 2022.
"Smart Selecta Duet—Your Smart Selection for Glaucoma Care," Product Brochure, pp. 1-6, The Lumenis Group of Companies, year 2018.
Root, "How to perform a Laser Iridotomy (Video)," pp. 1-14, year 2010, as downloaded from https://timroot.com/how-to-perform-a-laser-iridotomy-video/.
AU Application # 2022211843 Office Action dated Sep. 27, 2023.
AU Application # 2021311097 Office Action dated Sep. 28, 2023.
U.S. Appl. No. 17/427,926 Office Action dated Oct. 17, 2023.
JP Application # 2021536316 Office Action dated Oct. 24, 2023.
JP Application # 2020561860 Office Action dated Oct. 31, 2023.
JP Application # 2021516473 Office Action dated Nov. 7, 2023.
SG Application # 11202010437T Office Action Dec. 5, 2023.
U.S. Appl. No. 17/735,153 Office Action dated Dec. 18, 2023.
U.S. Appl. No. 17/136,052 Office Action dated Dec. 22, 2023.
U.S. Appl. No. 17/427,926 Office Action dated Dec. 22, 2023.
International Application # PCT/IB2023/060104 Search Report Dec. 26, 2023.
CN Application # 2019800436416 Office Action dated Aug. 17, 2022.
U.S. Appl. No. 16/935,236 Office Action dated Sep. 15, 2022.
U.S. Appl. No. 16/420,194 Office Action dated Aug. 5, 2022.
EP Application # 21885460.2 Search Report dated Aug. 26, 2024.
EP Application # 19830473.5 Office Action dated Sep. 3, 2024.
U.S. Appl. No. 17/273,323 Office Action dated Oct. 30, 2024.
U.S. Appl. No. 17/427,926 Office Action dated Aug. 27, 2024.
CN Office Action 1st Office Action, CN Application No. 202211655204.X, dated Dec. 24, 2025.
Notice of Reasons for Rejection, Japanese Patent Application No. 2024-114385, dated Sep. 30, 2025.
Chinese First Office Action, Patent Application No. 202180037579.7, dated Jul. 30, 2025.
Japanese Notice of Reasons for Rejection, Patent Application No. 2022-567443, dated Sep. 9, 2025.
Non-Final Office Action, U.S. Appl. No. 17/627,701, dated Sep. 24, 2025.
Australian Examination Report, Patent Application No. 2024205587, dated Oct. 2, 2025.

* cited by examiner

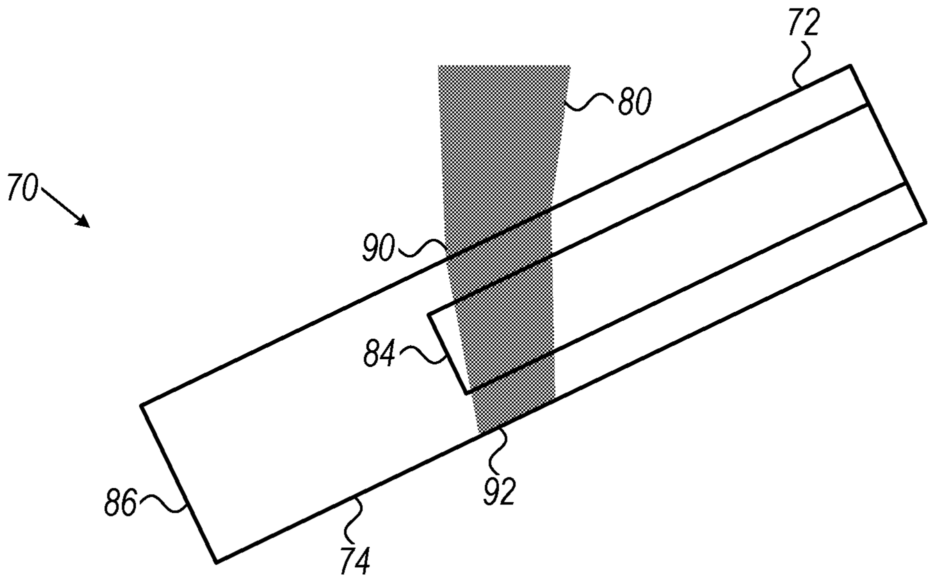
FIG. 4
FIG. 5A
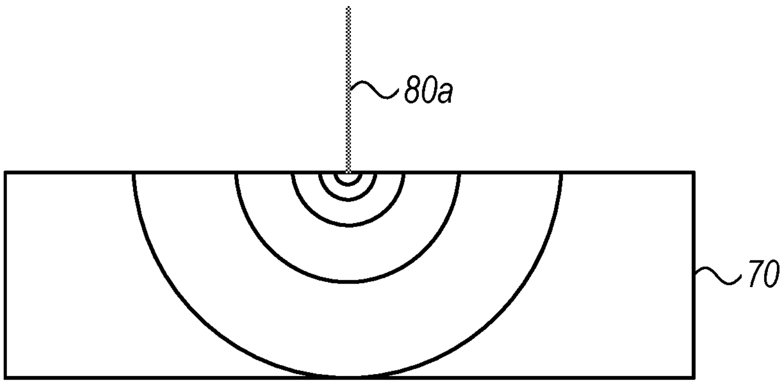
FIG. 5B
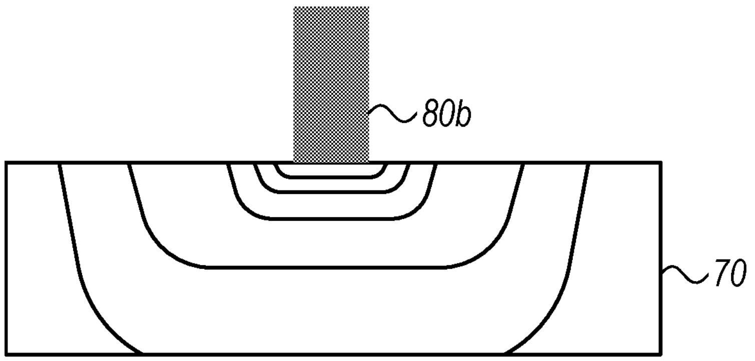

SELECTIVE LASER STIMULATION OF CORNEAL STEM CELLS

CROSS-REFERENCE TO RELATED APPLICATION

This application claims the benefit of U.S. Provisional Patent Application 62/899,162, filed Sep. 12, 2019, which is incorporated herein by reference.

FIELD OF THE INVENTION

The present invention relates generally to methods and apparatus for treatment of the eye, and particularly to treating conditions of the cornea.

BACKGROUND

The corneal epithelium consists of a few layers of cells on the anterior surface of the eye. These cells are almost continuously exposed and thus are constantly replaced. The cornea is the most highly innervated tissue in the body. Consequently, any disturbance of its epithelial surface leads to symptoms such as pain and discomfort, which may be severe. Furthermore, the corneal epithelium and its tear layer coverage are responsible for the proper optical transparency of the eye.

Dry eye syndrome occurs when either the eye does not produce enough tears or when the tears evaporate too quickly. It affects 5-34% of people to some degree, and up to 70% among older people. Symptoms of dry eye include irritation, redness, discharge, and easily fatigued eyes. More serious cases can lead to blurred vision and even corneal scarring.

The corneal endothelium lines the inner surface of the cornea and is responsible for the transparency of the tissue. Defects in the endothelium, whether due to diseases or trauma, can lead to corneal swelling and visual impairment.

Light can act on different mechanisms within cellular tissue to stimulate or suppress biological activity, in a process commonly referred to as photobiomodulation (PBM) or low light level therapy (LLLT). Therapy of this sort has been proposed for treatment of various conditions of the eye, although its clinical efficacy has not been conclusively established. For example, U.S. Patent Application Publication 2016/0067087 describes a wearable ophthalmic phototherapy device and associated treatment methods to expose an eye to selected multi-wavelengths of light to promote the healing of damaged or diseased eye tissue. The device includes a frame having a front piece and two earpieces extending from the front piece; and at least one light source producing a light beam having a therapeutic wavelength and disposed within or on the frame.

As another example, U.S. Pat. No. 9,192,780 describes a system and method for treatment of cells and, in particular, visual pathway disorders using photomodulation and/or photorejuvenation, particularly of retinal epithelial cells. The process of treating retinal cells to reduce or reverse the effects of visual pathway disorders employs a narrowband source of multichromatic light applied to the retinal cells to deliver a very low energy fluence.

SUMMARY

Embodiments of the present invention that are described hereinbelow provide improved apparatus and methods for treatment of the eye.

There is therefore provided, in accordance with an embodiment of the invention, apparatus for ophthalmic treatment, including an optical unit, which includes a camera, which is configured to capture an image of an eye of a patient, a laser, which is configured to emit pulses of laser radiation, and beam conditioning and scanning optics, which are configured to focus and direct the laser radiation to impinge on an anterior surface of the eye. A controller is configured to analyze the image so as to identify a limbus of the eye, and to control the optical unit so that the laser radiation impinges on a set of one or more locations on the anterior surface of the eye that are in a vicinity of the limbus with a pulse duration that is less than 1 μs and an energy that is less than 5 mJ per pulse, whereby the laser radiation stimulates stem cells at the one or more locations.

In a disclosed embodiment, the laser radiation is focused to impinge on each of the one or more locations with a beam diameter no greater than 1 mm. Additionally or alternatively, the pulse duration is less than 100 ns and may be less than 10 ns or even less than 5 ns. Further additionally or alternatively, the energy per pulse is less than 3 mJ. Typically, the laser radiation is focused to impinge on each of the one or more locations with a fluence less than 0.4 J/cm$^2$.

In some embodiments, the controller is configured to actuate the laser so as to apply multiple pulses to each of the one or more locations. In a disclosed embodiment, the multiple pulses include no more than 200 pulses at each location, and possibly no more than 100 pulses at each location. Additionally or alternatively, the multiple pulses deliver the laser radiation with a cumulative energy that is no greater than 100 mJ at each location and may be no greater than 70 mJ or even no greater than 40 mJ.

In a disclosed embodiment, the one or more locations on the anterior surface of the eye are displaced by at least 1 mm from the limbus and possibly by at least 2 mm from the limbus.

Additionally or alternatively, the beam conditioning and scanning optics are configured to direct the laser radiation to impinge on the anterior surface of the eye at an oblique angle relative to a direction of an optical axis of the eye. In one embodiment, the beam conditioning and scanning optics include a ring mirror, which is positioned around the optical axis of the eye so as to reflect the beam toward multiple locations in the vicinity of the limbus at oblique angles.

There is also provided, in accordance with an embodiment of the invention, apparatus for ophthalmic treatment, including an optical unit as described above. A controller is configured to analyze the image so as to identify a limbus of the eye, and to control the optical unit so that the laser radiation impinges on a set of one or more locations on the anterior surface of the eye in a vicinity of the limbus with a pulse duration that is between 1 ms and 500 ms and an energy that is less than 100 mJ per pulse, whereby the laser radiation stimulates stem cells at the one or more locations.

In some embodiments, the pulse duration is less than 50 ms and may be less than 10 ms or even less than 5 ms. Additionally or alternatively, the energy per pulse is less than 50 mJ and may be less than 5 mJ. Typically, the laser radiation is focused to impinge on each of the one or more locations with a fluence less than 30 J/cm$^2$.

In some embodiments, the controller is configured to actuate the laser so as to apply multiple pulses to each of the one or more locations. In a disclosed embodiment, the multiple pulses include no more than no more than 2000 pulses at each location and possibly no more than 500 pulses at each location or even no more than 200 pulses at each location. Additionally or alternatively, the multiple pulses deliver the laser radiation with a cumulative energy that is no greater than 10 J at each location and possibly no greater than 1 J or even no greater than 400 mJ.

There is additionally provided, in accordance with an embodiment of the invention, a method for ophthalmic treatment, which includes identifying a limbus of an eye of a patient, and directing pulses of laser radiation to impinge on a set of one or more locations on an anterior surface of the eye in a vicinity of the limbus with a pulse duration that is less than 1 μs and an energy that is less than 5 mJ per pulse, so as to stimulate stem cells at the one or more locations.

There is further provided, in accordance with an embodiment of the invention, a method for ophthalmic treatment, which includes identifying a limbus of an eye of a patient, and directing pulses of laser radiation to impinge on a set of one or more locations on an anterior surface of the eye in a vicinity of the limbus with a pulse duration that is less than 100 ms and an energy that is less than 100 mJ per pulse, so as to stimulate stem cells at the one or more locations.

There is moreover provided, in accordance with an embodiment of the invention, apparatus for treating an eye of a patient. The apparatus includes an optical unit, including a laser, which is configured to emit laser radiation, one or more mirrors positioned around an optical axis of the eye, and beam conditioning and scanning optics, which are configured to focus and direct the laser radiation to reflect from the one or more mirrors so as to impinge on an anterior surface of the eye at an oblique angle relative to the optical axis. A controller is configured to control the optical unit so that the laser radiation impinges on the eye at the oblique angle in a set of one or more locations in a vicinity of the limbus with a fluence selected so as to stimulate stem cells at the one or more locations.

In a disclosed embodiment, the one or more mirrors include a ring mirror, which surrounds the optical axis.

In one embodiment, the controller is configured to control the optical unit so that the laser radiation impinges on and stimulates the stem cells in an epithelium of the eye. Alternatively or additionally, the controller is configured to control the optical unit so that the laser radiation impinges on and stimulates the stem cells in a stroma of the eye. Further additionally or alternatively, the controller is configured to control the optical unit so that the laser radiation impinges on and stimulates the stem cells in an endothelium of the eye.

There is furthermore provided, in accordance with an embodiment of the invention, a method for ophthalmic treatment, which includes placing a gonioscope in contact with a cornea of an eye of a patient. Pulses of laser radiation are directed through the gonioscope to reflect from a side mirror surface of the gonioscope and then to pass obliquely through the cornea and impinge on endothelial tissue in a vicinity of a trabecular meshwork of the eye with a pulse energy and duration selected so as to stimulate stem cells in the endothelial tissue.

In some embodiments, the pulses have a pulse duration that is less than 1 μs and an energy that is less than 0.1 mJ per pulse. In a disclosed embodiment, directing the pulses includes controlling the laser radiation to impinge on the endothelial tissue with a fluence no greater than 0.1 J/cm$^2$. Additionally or alternatively, the pulses have a pulse duration that is between 1 and 500 ms and a fluence no greater than 10 J/cm$^2$.

The present invention will be more fully understood from the following detailed description of the embodiments thereof, taken together with the drawings in which:

BRIEF DESCRIPTION OF THE DRAWINGS

FIG. 4 is a schematic sectional idealized illustration of a limbal area of an eye showing propagation of a laser beam through the area, in accordance with an embodiment of the invention;

FIGS. 5A and 5B are schematic idealized sectional illustrations of tissue in an eye showing distributions of optical fluence under irradiation by laser beams of different focal properties, in accordance with an embodiment of the invention;

DETAILED DESCRIPTION OF EMBODIMENTS

Overview

Figure 1:
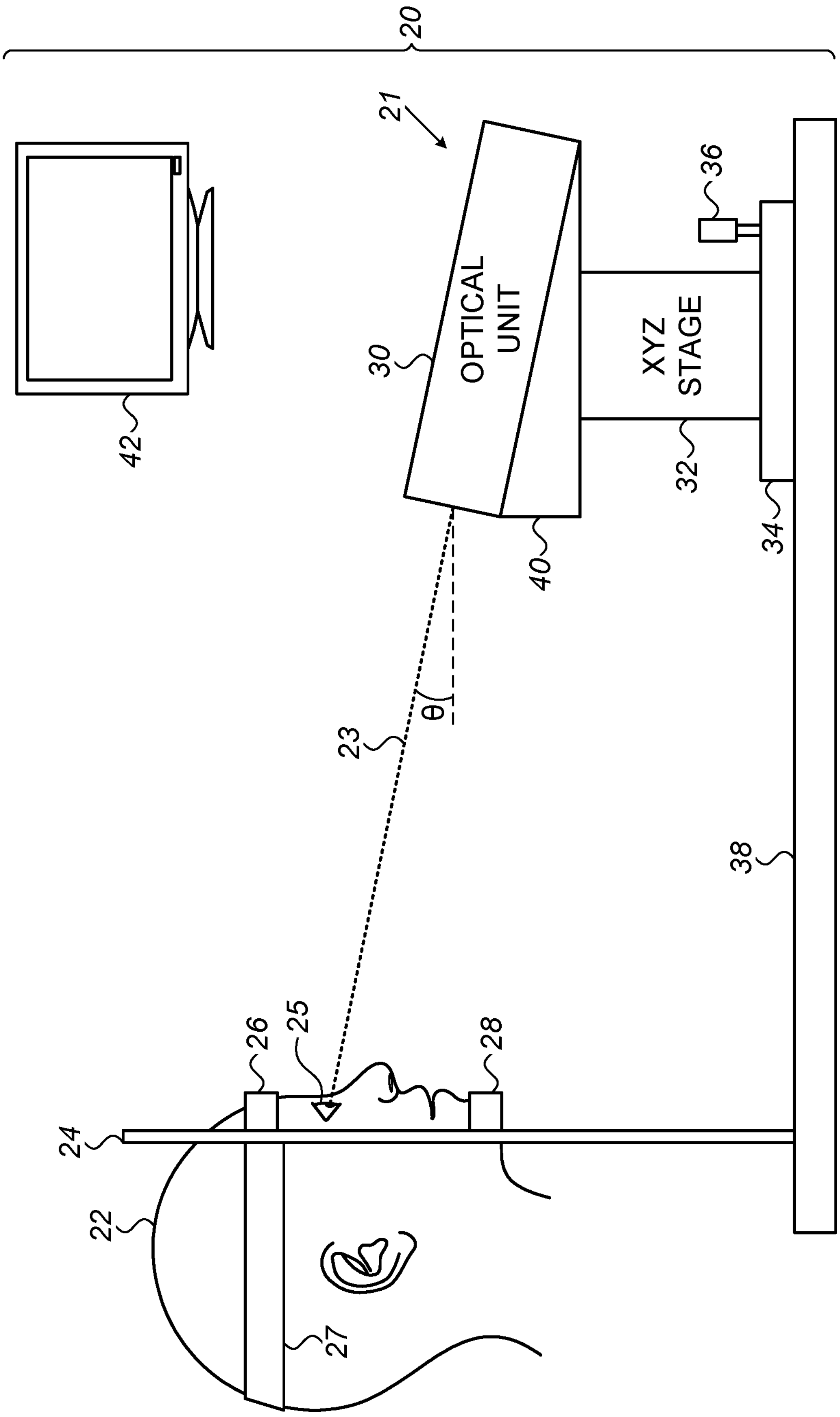
FIG. 1 is schematic side view of a system for ophthalmic treatment, in accordance with an embodiment of the invention.

Stem cells play important roles in homeostasis and repair of tissues in the eye. For example, inadequate stem cell activity appears to be one of the causes of dry eye and other pathologic conditions of the cornea. Stimulation of stem cell activity can be an effective treatment for such conditions.

LLLT using visible or infrared laser radiation has been found to stimulate stem cell activity in various tissues in the body. This sort of therapy typically uses CW laser radiation at moderate energy levels. Application of such radiation to the eye, however, can have serious unintended consequences, including transient and possibly permanent damage to the retina and other physiological structures. For example, laser irradiation of the region around the limbus with sufficient intensity has been shown to reduce intraocular pressure, as described in U.S. Pat. No. 10,702,416, whose disclosure is incorporated herein by reference. This effect is helpful in treating glaucoma, but it can lead to dangerously low pressure if applied to patients whose initial intraocular pressure is in the normal range.

In response to these needs and constraints, embodiments of the present invention that are described herein provide apparatus and methods for treatment of the cornea using pulsed laser radiation, with pulse parameters chosen specifically to stimulate cornea stem cells while minimizing undesired collateral effects. The disclosed techniques can be adapted to stimulate the stem cells in any and all of the layers of the cornea, including the epithelium, stroma, and endothelium. They are particularly effective in stimulating epithelial stem cell activity and thus in treating conditions of the corneal epithelium, such as dry eye. In an alternative embodiment, corneal endothelial stem cells are activated by this sort of laser irradiation.

The embodiments that are described hereinbelow use an optical unit comprising a camera, which captures images of the eye of a patient. A laser in the optical unit emits pulses of laser radiation, which are focused and directed by beam conditioning and scanning optics to impinge on the anterior surface of the eye. A controller analyzes the image so as to identify the limbus of the eye, and then controls the optical unit so that the laser radiation impinges on a set of one or more locations on the anterior surface of the eye in the vicinity of the limbus, including locations that are displaced by a predefined radial distance of at least 1 mm from the limbus, and possibly by 2, 3 or even 4 mm. These are locations at which stem cell stimulation can be effective while avoiding undesired effects on underlying structures. Alternatively, the locations to be irradiated are identified by other methods of image analysis and eye tracking that are known in the art, for example pupil tracking or pattern recognition.

There are two regimes of laser pulse parameters that the inventors have found to be effective in stimulating corneal stem cells (particularly in the epithelium), while minimizing other undesired effects. In some embodiments, the laser radiation impinges on the eye with a pulse duration that is less than 1 μs and an energy that is less than 5 mJ per pulse. In alternative embodiments, the pulse duration can range up to 100 ms, with a pulse energy up to 100 mJ per pulse. The fluence of laser radiation on the eye in each pulse is held below a predefined limit, for example less than 2 J/cm$^2$ in the short pulse domain (less than 1 μs) or less than 120 J/cm$^2$ in the longer pulse domain (up to 100 ms). The cumulative energy applied to each location is similarly held below a limit that is chosen so as to provide substantial stem cell stimulation while avoiding collateral effects.

In either case, the laser beam is typically focused to a small spot at each of the locations, for example with a beam diameter of 1 mm or less. The use of a small spot size of this sort is advantageous particularly in concentrating the beam intensity, and hence the stimulation of stem cells, in the epithelial layer. The intensity reaching the endothelium, which can affect structures such as the trabecular meshwork, is much smaller.

Some embodiments of the present invention make use of the inherent scattering properties of the tissue in the limbus. Simulations have shown that only approximately 11% of the laser energy that is incident on the limbus reaches the underlying trabecular meshwork. A clinical study conducted by the inventors showed that irradiation of the trabecular meshwork by laser pulses having a pulse energy of 0.8 mJ on the outer surface of the limbal region was effective at reducing intraocular pressure. A dose response has been observed in this sort of irradiation, meaning that higher energies result in greater pressure reduction. Thus, in some embodiments of the present invention, laser pulse energies below 0.8 mJ are used so that only the corneal epithelial and stromal stem cells are stimulated. Further energy reduction can be useful in ensuring that endothelial stem cells are not stimulated, so as to avoid undesired reduction of the intraocular pressure. In alternative embodiments, however, the energy and direction of the incident laser beam are chosen so that the endothelial stem cells are significantly stimulated.

There appear to be multiple pathways by which laser radiation can stimulate stem cells in the eye, including, but not limited to, thermal heating, nonlinear absorption processes, and photo-acoustic processes. Nanosecond laser pulses require about two orders of magnitude less fluence than millisecond-range pulses to achieve similar levels of stem cell stimulation. At the levels of fluence used in embodiments of the present invention, the attenuation of the laser energy propagating through the limbus is independent of pulse duration and energy, such that longer laser pulses with higher energy will also be attenuated by approximately 11%.

System Description

Figure 2:
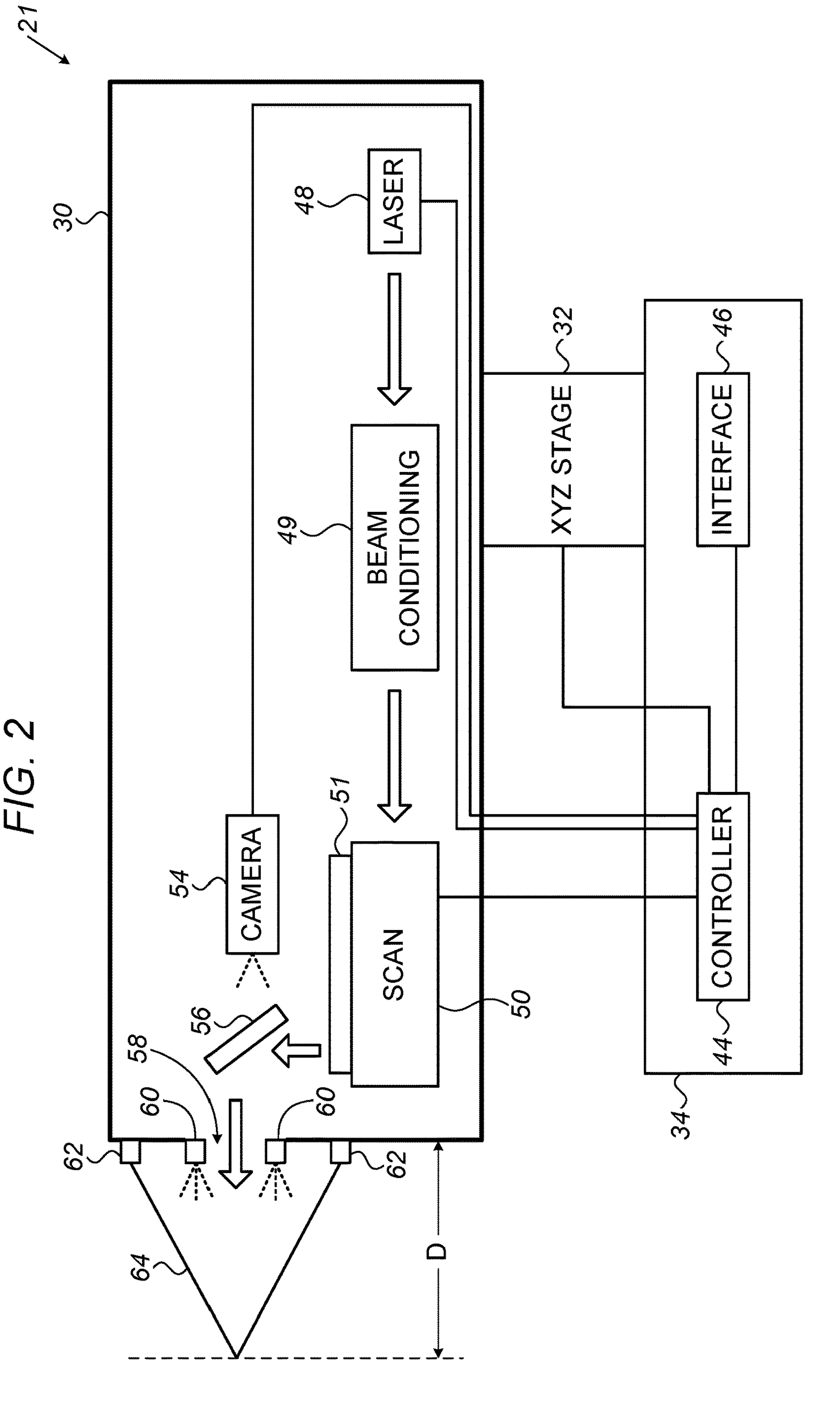
FIG. 2 is a block diagram that schematically shows details of a laser treatment device in the system of FIG. 1, in accordance with an embodiment of the invention.

Reference is now made to FIGS. 1 and 2, which schematically illustrate a system 20 for ophthalmic treatment using LLLT, in accordance with an embodiment of the invention. FIG. 1 is a side view of the system, while FIG. 2 is a block diagram showing details of a laser treatment device 21 in system 20. System 20 is similar in its design to a system for direct laser selective trabeculoplasty that is described in PCT International Publication WO 2020/008323, whose disclosure is incorporated herein by reference. In the present embodiment, however, the laser beam parameters and treatment modality in system 20 are specifically adapted for targeted stimulation of stem cells, while minimizing the effect of the laser beam on the trabecular meshwork.

Treatment device 21 comprises an optical unit 30, comprising a radiation source 48, such as a laser, which outputs a beam of pulsed radiation toward an eye 25 of a patient 22. Optical unit 30 further comprises beam-conditioning optics 49, for adjusting the focal properties of the laser beam, so that the beam is incident on the surface of eye 25 with the desired spot size and energy. A scanner 50 directs the beam toward the desired target location for the LLLT treatment. Scanner 50 may comprises, for example, one or more galvanometric mirrors or any other suitable type of optical scanner that is known in the art. An F-theta lens 51 can be used to preserve uniform beam properties over the range of the scan. A beam combiner 56 directs the laser beam through an aperture 58 at the front of optical unit 30 toward eye 25.

Optical unit 30 further comprises a camera 54, which acquires images of eye 25 via beam combiner 56 before and during the LLLT procedure. In the pictured embodiment, to aid in imaging of the eye, optical unit 30 comprises an illumination source 60 comprising, for example, one or more light emitting diodes (LEDs), such as a ring of LEDs surrounding aperture 58. A controller 44 processes the images output by camera 54 and, based on the images, controls radiation source 48, as well as optics 49 and scanner 50. Specifically, for purposes of the LLLT, the controller identifies the limbus of eye 25, and then aims the laser beam to direct pulses of radiation of the desired fluence toward locations in the vicinity of the limbus, meaning locations that are on the limbus or are displaced radially from the limbus by an appropriate distance along the anterior surface of the eye. The limbus can be identified using any suitable method of image processing that is known in the art, for example by finding the circular edge between the iris and sclera in the image. Methods for locating the limbus are described further in the above-mentioned U.S. Pat. No. 10,702,416.

Typically, as a preliminary step before beginning treatment, the user of system 20, such as an ophthalmologist, positions optical unit 30 at a predefined distance D from the eye using a control mechanism 36, such as a joystick. To facilitate this positioning, optical unit 30 may comprise multiple beam emitters 62 (comprising, for example, laser diodes), which direct respective range-finding beams 64 toward the eye. Beams 64 form a composite pattern on the eye, which enables the user to ascertain that the optical unit is at the predefined distance.

Optical unit 30 is mounted on an XYZ stage 32, which is controlled by control mechanism 36. Using control mechanism 36, the user of system 20 positions the optical unit at the appropriate position prior to treating the eye of the patient. In some embodiments, XYZ stage 32 comprises one or more motors, and control mechanism 36 is connected to the XYZ stage via interface circuitry 46 and controller 44. In other embodiments, XYZ stage 32 is controlled manually by manipulating the control mechanism.

During operation, patient 22 places his head on a headrest 24, which is mounted on a horizontal surface 38, such as a tray or tabletop. Headrest 24 comprises a forehead rest 26 and a chinrest 28. During the LLLT procedure, patient 22 presses his forehead against forehead rest 26 while resting his chin on chinrest 28. An immobilization strap 27 secures the patient's head from behind and thus keep the patient's head pressed against the headrest.

In the pictured embodiment, a base unit 34 of device 21 is mounted on surface 38, and XYZ stage 32 is mounted on base unit 34. In such embodiments, controller 44 and interface circuitry 46 may be contained within the base unit. In other embodiments, the XYZ stage is mounted directly on surface 38.

It can be advantageous, as shown in FIG. 1, that while irradiating the patient's eye, optical unit 30 is directed obliquely upward toward the eye while the eye gazes obliquely downward toward the optical unit, i.e., an optical path 23 between the eye and the optical unit is oblique, rather than horizontal. For example, optical path 23 may be oriented at an angle θ of between five and twenty degrees, in order to reduce occlusion of the patient's eye by the patient's upper eyelid and associated anatomy. Optionally, for additional exposure of the eye, a finger, a speculum, or another tool may be used to retract one or both of the eyelids. In the embodiment shown in FIG. 1, the oblique orientation of optical path 23 is achieved by mounting optical unit 30 on a wedge 40, which is mounted on XYZ stage 32. Alternatively or additionally, the patient's head may be intentionally tilted in headrest 24.

System 20 optionally comprises a monitor 42, which displays the images of eye 25 that are acquired by camera 54 and enables the user to verify proper alignment and operation of the system. Monitor 42 can be connected directly to controller 44 over a wired or wireless communication interface or indirectly via an external processor, such as a processor belonging to a standard computer.

The configuration of system 20 and treatment device 21 that is shown in FIGS. 1 and 2 is presented and described here by way of example only. The principles of LLLT treatment that are described herein may alternatively be implemented, mutatis mutandis, in other system configurations that are capable of irradiating the patient's eye at the appropriate locations with suitable beam parameters, as defined herein. All such alternative implementations are considered to be within the scope of the present invention.

Controller 44 typically comprises a general-purpose microprocessor, which is programmed in software to carry out the functions described herein and has appropriate interfaces for communicating with the other elements of system 20. The software may be downloaded to the controller in electronic form, over a network, for example. Alternatively or additionally, the software may be provided and/or stored on non-transitory tangible media, such as magnetic, optical, or electronic memory. Such software, when provided to the controller, produces a machine or special-purpose computer, configured to perform the tasks described herein. Alternatively or additionally, at least some of the functions of controller 44 may be implemented in dedicated or programmable hardware logic, for example using one or more Application-Specific Integrated Circuits (ASICs) or Field-Programmable Gate Arrays (FPGAs).

Therapeutic Modalities

Figure 3:
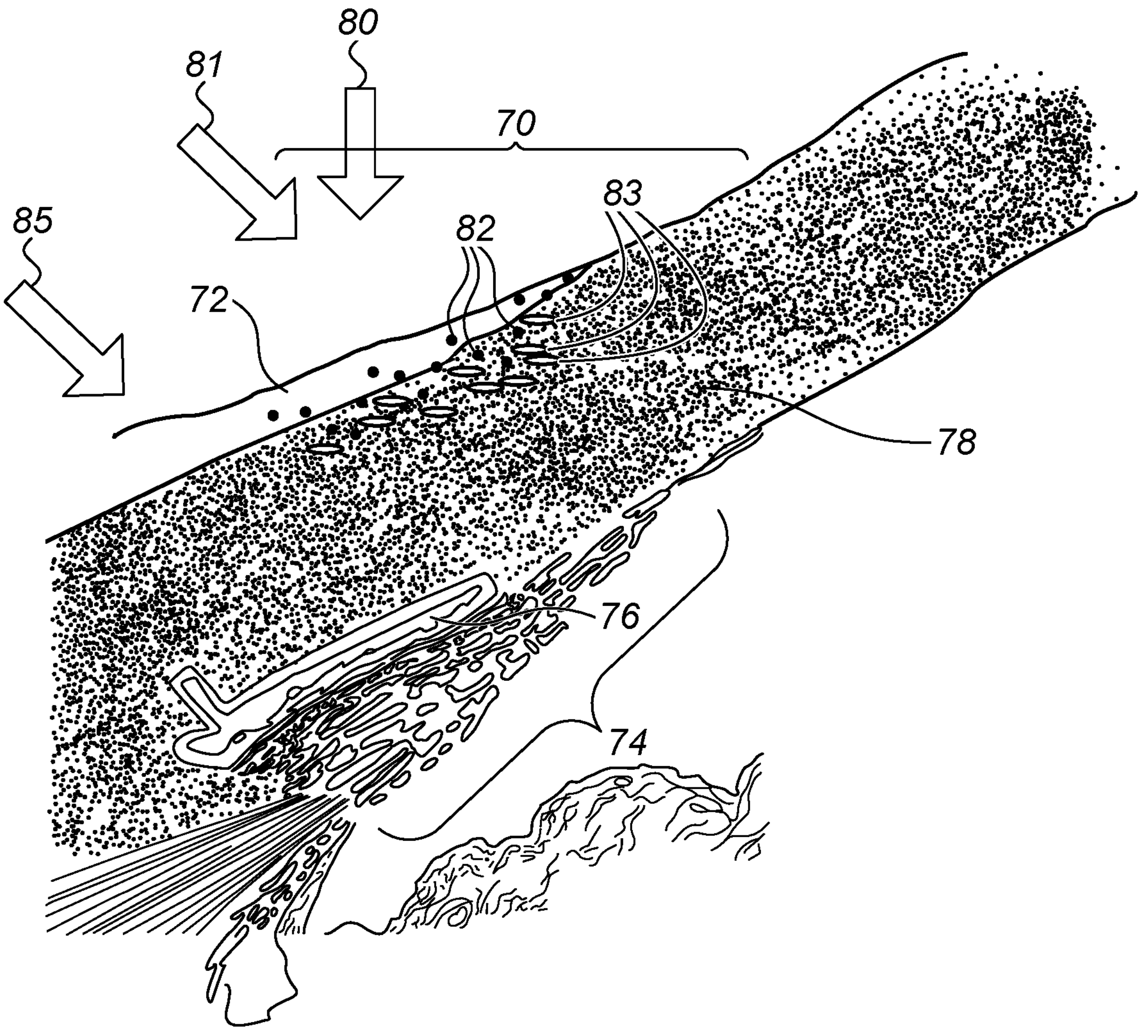
FIG. 3 is a schematic sectional illustration of structures in an eye under treatment by laser radiation, in accordance with an embodiment of the invention.

FIG. 3 is a schematic sectional illustration of structures in a limbal area 70 of an eye under treatment by laser radiation 80, in accordance with an embodiment of the invention. (The limbus itself falls roughly in the center of this area.) Limbal area 70 includes a corneal epithelium 72, containing epithelial stem cells 82. Laser radiation 80 is generated, for example, by optical unit 30 in system 20, as described above. The beam parameters of laser radiation 80, including the number of laser pulses, the energy and duration per pulse, and the focal spot size of the laser beam on epithelium 72, are chosen so as to stimulate stem cells 82 selectively.

Beneath the epithelium, the cornea contains a stroma 78, containing stromal stem cells 83, and an endothelium 74, including the trabecular meshwork and Schlemm's canal 76 (among other structures), as well as endothelial stem cells (not shown in the figure). In the present embodiment, the laser beam parameters are chosen so as to minimize penetration of laser energy into these inner layers and thus avoid stimulation of the stem cells in these layers. This selectivity may be enhanced, for example, by directing laser radiation 81 to impinge on the area of epithelial stems cells 82 in an oblique direction. (The term "oblique," as used in the present description and in the claims, means that the laser beam impinges on the eye at an angle of at least 5° relative to the direction of the optical axis of the eye, i.e., an axis passing through the center of the pupil to the macula. In some embodiments, the laser beam may impinge on the eye at an angle of 10° or more.)

In alternative embodiments, however, the laser beam parameters may be modified, for example by increasing the fluence and/or the focal spot size, in order to stimulate the stem cells in stroma 78, as well as in endothelium 74. Increasing the energy dosage sufficiently to affect the trabecular meshwork can also reduce intraocular pressure, as described in the above-mentioned U.S. Pat. No. 10,702,416, in conjunction with the effect of the laser radiation on the endothelial stem cells. Additionally or alternatively, laser radiation 85 may be directed to impinge on the eye at the edge of limbal region 70, at an oblique angle selected so as to stimulate the endothelial stem cells, while avoiding the epithelial and stromal stem cells.

FIG. 4 is a schematic, idealized sectional illustration of limbal area 70 of an eye showing propagation of unscattered laser radiation 80 through the area, in accordance with an embodiment of the invention. Laser radiation 80 impinges on an entrance spot 90 at a target location on epithelium 72, at the anterior surface of the eye. As noted earlier, spot 90 is typically no greater than 1 mm in diameter, and may be smaller. The radiation passes through a cornea 84 of the eye and impinges on endothelium 74 at an exit spot 92.

The intensity of the laser radiation drops sharply, typically by more than 90%, between entrance spot 90 and exit spot 92, due mainly to scattering of the radiation within the limbal tissues. Due to these scattering properties, the stimulation of the epithelial stem cells can be as much as twenty times stronger (or even more, depending on the wavelength of light and the specific patient eye anatomy) than that of the endothelial stem cells. This differential effect can be enhanced still more by focusing radiation 80 sharply onto entrance spot 90.

FIGS. 5A and 5B are schematic sectional illustrations of tissue in limbal area 70 of an eye, showing distributions of optical fluence under irradiation by laser beams 80*a* and 80*b* of different focal properties, in accordance with an embodiment of the invention. Beam 80*a* is sharply focused onto the anterior surface of the eye, whereas beam 80*b* has a much larger spot size. The contours in the figures illustrate the relative decrease in fluence as the beams propagate through the tissue. The larger spot size of beam 80*b* increases the relative fluence reaching the endothelium and thus enables greater stimulation of internal structures, such as the stromal and endothelial stem cells.

In some embodiments, optical unit 30 (FIG. 1) is operated to emit pulses having a pulse duration that is less than 1 μs and an energy that is less than 5 mJ per pulse. Alternatively, the pulses may be still shorter, for example less than 100 ns. In some cases, it is advantageous that the pulse durations be less than 10 ns or even 5 ns. Additionally or alternatively, the pulse energy may be smaller, for example less than 3 mJ. Typically, the laser radiation is focused to impinge on each of the treated locations with a fluence that is less than 0.4 $J/cm^2$. Controller 44 typically actuates laser 48 and controls scanner 50 to apply sequences of multiple pulses at each of the treated locations on the anterior surface of the eye. Typically, 200 pulses at each location provide sufficient therapeutic effect, and 100 pulses or less may be preferred in order to accelerate the treatment and reduce collateral effects. For these same reasons, the cumulative energy that is delivered by optical unit 30 to each such location is no greater than 100 mJ, and may be less than 70 mJ or even 40 mJ.

In other embodiments, optical unit 30 may apply pulses of lower peak power but higher total energy to the anterior surface of the eye. In such embodiments, laser 48 emits pulses having a pulse duration that is greater than 1 ms but less than 500 ms and an energy that is less than 100 mJ per pulse. Alternatively, the pulses may be shorter, for example less than 100 ms. In some cases, it is advantageous that the pulse durations be less than 50 ms, and possibly less than 10 ms or even 5 ms. Additionally or alternatively, the pulse energy may be smaller, for example less than 50 mJ or possibly less than 5 mJ. Typically, the laser radiation is focused to impinge on each of the treated locations with a fluence that is less than 30 $J/cm^2$. Controller 44 typically actuates laser 48 and controls scanner 50 to apply sequences of multiple pulses at each of the treated locations, typically no more than 2000 pulses at each location. Alternatively, as in the preceding embodiment, 500 pulses or less, or even as few as 200 pulses at each location, may be preferred in order to accelerate the treatment and reduce collateral effects. The cumulative energy that is delivered by optical unit 30 to each such location is no greater than 10 J, and may be less than 1 J or even 400 mJ.

Alternative Embodiments

Figure 6:
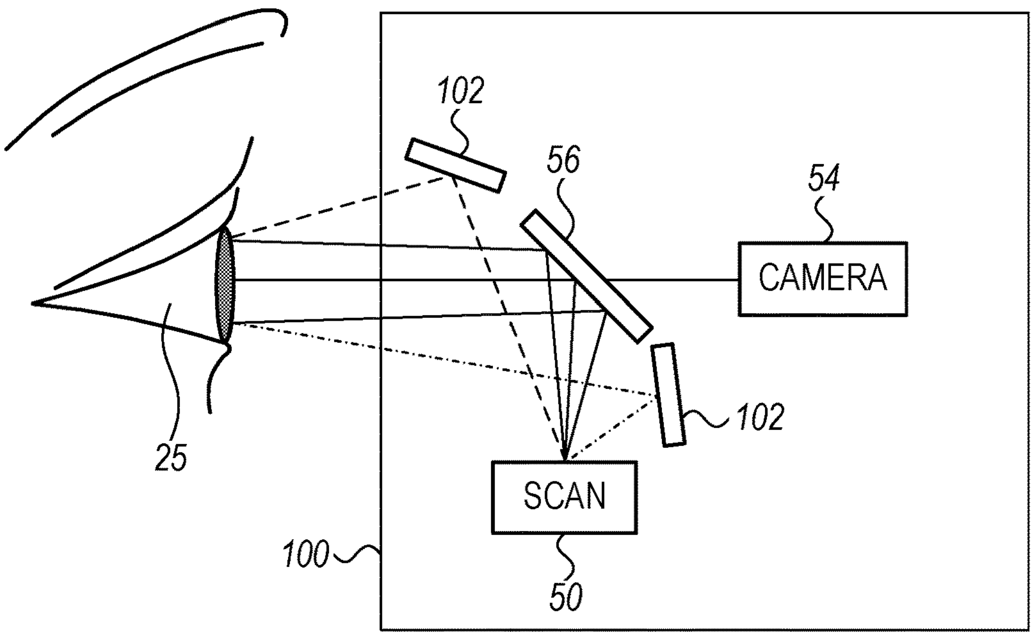
FIGS. 6 and 7 are schematic sectional views of systems for ophthalmic treatment, in accordance with alternative embodiments of the invention.
Figure 7:
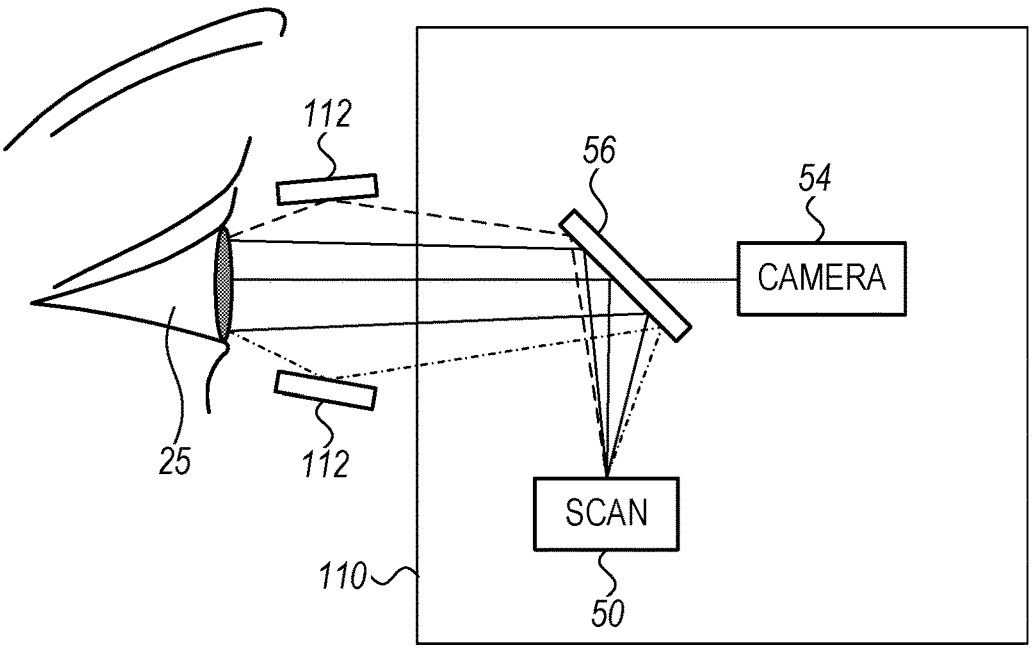

FIGS. 6 and 7 are schematic sectional views of systems 100 and 110 for ophthalmic treatment, respectively, in accordance with alternative embodiments of the invention. These systems are similar to system 20, as shown in FIGS. 1 and 2, but include additional optical components to facilitate directing the laser radiation to impinge on the anterior surface of the eye at an oblique angle relative to the direction of the optical axis of the eye. The laser radiation may be pulsed, as described above, or continuous wave (CW). As explained earlier, this sort of oblique-angle irradiation is useful in selectively stimulating the stem cells in a particular layer of the cornea, such as the epithelial, stromal, or endothelial stem cells.

In system 100, a ring mirror 102 is positioned around the optical axis of the eye, surrounding the optical axis and beam combiner 56. In one embodiment, ring mirror 102 comprises a unitary ellipsoidal reflector. Alternatively, ring mirror 102 may comprise multiple mirror segments, for example flat segments, which are arranged to emulate the optical performance of an ellipsoid. In any case, when scanner 50 directs the laser beam toward ring mirror 102, the beam will be reflected toward the eye at an oblique angle relative to the optical axis.

In system 110, a ring mirror 112 is attached externally to the optical unit, similarly surrounding the optical axis of the eye. Ring mirror 112 may be constructed and mounted, for example, in the manner in which a frustum-shaped conduit is attached to the optical unit in PCT Patent Application PCT/IB2020/052020, filed Mar. 9, 2020, whose disclosure is incorporated herein by reference. In this case, too, when scanner 50 directs the laser beam toward ring mirror 112, the beam will be reflected toward the eye at an oblique angle relative to the optical axis.

Figure 8:
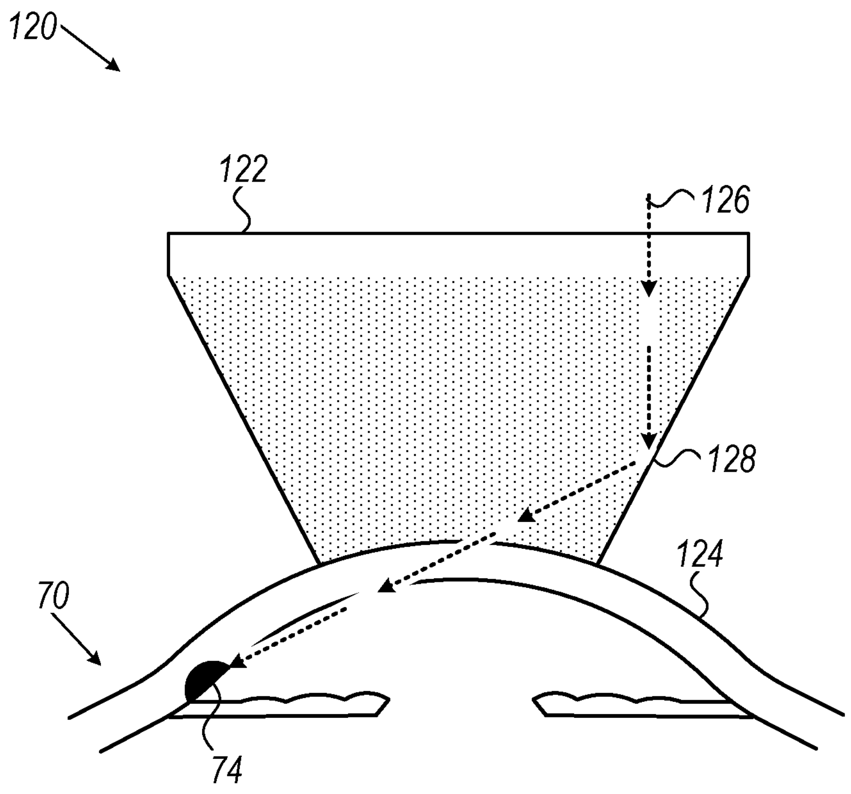
FIG. 8 is a schematic sectional illustration of apparatus for ophthalmic treatment, in accordance with yet another embodiment of the invention.

FIG. 8 is a schematic sectional illustration of apparatus 120 for ophthalmic treatment, in accordance with yet another embodiment of the invention. In this embodiment, a gonioscope 122 is held in contact with a cornea 124 of an eye. A laser beam 126 is directed to reflect from a side minor surface 128 of gonioscope 122, and thus to pass obliquely through the transparent area of cornea 124 and impinge on endothelial tissue in the vicinity of trabecular meshwork 74. This sort of optical approach is used in some methods of laser trabeculoplasty that are known in the art.

In the present embodiment, however, the laser pulse energy is far lower than the threshold for effective trabeculoplasty: For example, laser beam 126 may comprise pulses with a pulse duration that is less than 1 μs and an energy that is less than 0.1 mJ per pulse, with a fluence no greater than 0.1 $J/cm^2$. Alternatively, the pulses may have a pulse duration between 1 and 500 ms and fluence no greater than 10 $J/cm^2$. These laser pulses will stimulate the endothelial stem cells. Due to the high angle of incidence of the laser beam and the high scattering loss of the tissue in limbal area 70, relatively little laser energy will penetrate outward from the corneal endothelium to the epithelial and stromal stem cells. In this case, the endothelial stem cells will be stimulated selectively.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for treating an eye of a patient, the apparatus comprising:

an optical unit, comprising:

a laser, which is configured to emit laser radiation, wherein the laser radiation is pulsed, with a pulse duration that is less than 1 us and an energy that is less than 5 mJ per pulse;

one or more mirrors positioned around an optical axis of the eye; and beam conditioning and scanning optics, which are configured to focus and direct the laser radiation to reflect from the one or more mirrors so as to impinge on an anterior surface of the eye at an oblique angle relative to the optical axis with a beam diameter no greater than 1 mm; and a controller, which is configured to control the optical unit so that the laser radiation impinges on the eye at the oblique angle in a set of one or more locations in a vicinity of the limbus with a fluence selected so as to stimulate stem cells at the one or more locations.

2. The apparatus according to claim 1, wherein the one or more mirrors comprise a ring mirror, which surrounds the optical axis.

3. The apparatus according to claim 1, wherein the controller is configured to control the optical unit so that the laser radiation impinges on and stimulates the stem cells in a epithelium of the eye.

4. The apparatus according to claim 1, wherein the controller is configured to control the optical unit so that the laser radiation impinges on and stimulates the stem cells in a stroma of the eye.

5. The apparatus according to claim 1, wherein the controller is configured to control the optical unit so that the laser radiation impinges on and stimulates the stem cells in an endothelium of the eye.

6. The apparatus according to claim 1, wherein the pulse duration is less than 100 ns.

7. The apparatus according to claim 1, wherein the energy per pulse is less than 3 mJ.

8. The apparatus according to claim 1, wherein the laser radiation is focused to impinge on each of the one or more locations with a fluence less than 0.4 $J/cm^2$.

* * * * *